United States Patent
McGloin et al.

(10) Patent No.: US 12,216,192 B2
(45) Date of Patent: Feb. 4, 2025

(54) ANGULAR AND LINEAR MOVEMENT DETECTION AND COMPENSATION FOR USER EQUIPMENT

(71) Applicant: QUALCOMM Incorporated, San Diego, CA (US)

(72) Inventors: Justin Patrick McGloin, Los Altos, CA (US); Victor Kulik, San Jose, CA (US); Ana Londergan, Santa Clara, CA (US)

(73) Assignee: QUALCOMM Incorporated, San Diego, CA (US)

( * ) Notice: Subject to any disclaimer, the term of this patent is extended or adjusted under 35 U.S.C. 154(b) by 850 days.

(21) Appl. No.: 17/193,971

(22) Filed: Mar. 5, 2021

(65) Prior Publication Data

US 2022/0283287 A1    Sep. 8, 2022

(51) Int. Cl.
*G01S 13/58*    (2006.01)
*G01C 19/00*    (2013.01)
(Continued)

(52) U.S. Cl.
CPC ............ *G01S 13/583* (2013.01); *G01C 19/00* (2013.01); *G01C 21/1652* (2020.08);
(Continued)

(58) Field of Classification Search
CPC ........ G01S 13/583; G01S 7/354; G01S 13/88; G01S 7/40; G01S 13/343; G01S 13/5242;
(Continued)

(56) References Cited

U.S. PATENT DOCUMENTS

2020/0288060 A1    9/2020    Grenet
2022/0075049 A1*   3/2022    Åström ............... G01S 13/5242

FOREIGN PATENT DOCUMENTS

WO    WO-2020126051 A1    6/2020

OTHER PUBLICATIONS

Cardillo E., et al., "Vital Sign Detection and Radar Self-Motion Cancellation Through Clutter Identification", IEEE Transactions on Microwave Theory and Techniques, IEEE, USA, vol. 69, No. 3, Jan. 20, 2021 (Jan. 20, 2021), pp. 1932-1942, XP011842796, ISSN: 0018-9480, DOI: 10.1109/TMTT.2021.3049514 [retrieved on Mar. 4, 2021] the whole document.
(Continued)

*Primary Examiner* — Ankur Jain
(74) *Attorney, Agent, or Firm* — QUALCOMM Incorporated

(57) ABSTRACT

In some implementations, a user equipment (UE) may determine an angular motion using at least one gyroscope. The UE may adjust at least one measurement from at least one sensor that is associated with the UE and used to measure relative position, based at least in part on the angular motion. Additionally, in some implementations, the UE may determine at least one distance between the at least one sensor and an estimated grip associated with the UE, and determine at least one translation associated with the at least one sensor based at least in part on the angular motion and the at least one distance. Accordingly, the UE may adjust the at least one measurement by offsetting the at least one measurement based at least in part on the at least one translation.

36 Claims, 9 Drawing Sheets

(51) Int. Cl.
*G01C 21/16* (2006.01)
*G01P 15/08* (2006.01)
*H04W 4/02* (2018.01)
*H04W 4/38* (2018.01)

(52) U.S. Cl.
CPC ...... *G01P 15/08* (2013.01); *G06F 2200/1637* (2013.01); *H04W 4/026* (2013.01); *H04W 4/38* (2018.02)

(58) Field of Classification Search
CPC ..... G01S 13/86; G01C 19/00; G01C 21/1652; G01P 15/08; G06F 2200/1637; G06F 3/0346; H04W 4/026; H04W 4/38; H04W 76/19; H04W 4/14; H04W 4/16; H04W 88/06; H04W 88/10; A61B 5/002; A61B 5/05; A61B 5/1101; A61B 5/113; A61B 5/6898; A61B 5/7264; A61B 5/7475; A61B 2562/0219; A61B 5/1113; H04M 2203/654
USPC ....................................................... 455/90.1
See application file for complete search history.

(56) References Cited

OTHER PUBLICATIONS

International Search Report and Written Opinion—PCT/US2022/070170—ISA/EPO—Apr. 7, 2022.

\* cited by examiner

ANGULAR AND LINEAR MOVEMENT DETECTION AND COMPENSATION FOR USER EQUIPMENT

FIELD OF THE DISCLOSURE

Aspects of the present disclosure generally relate to motion compensation for user equipment and, for example, to detecting angular and linear movement to compensate for user equipment motion.

BACKGROUND

User equipment (UEs), such as smartphones, tablets, and other mobile computing devices often are required to reduce transmit power when in proximity to animate objects, particularly for 5G wavelength transmissions, such as millimeter wave (mmW) transmission. These reductions may be for safety reasons and may be mandated by government agencies, such as the Federal Communications Commission (FCC). UEs may use one or more technologies to detect nearby objects, such as infrared sensing, radio frequency radar, camera detection, and/or other similar techniques, and classify those objects as animate or inanimate (e.g., based at least in part on motions of those objects). The UEs may thus reduce transmit power based on detection and classification of nearby objects as animate.

SUMMARY

In some implementations, a method of movement detection performed by a user equipment (UE) includes determining an angular motion using at least one gyroscope of the UE; and adjusting at least one measurement from at least one sensor that is associated with the UE and used to measure relative position, based at least in part on the angular motion.

In some implementations, a UE includes a memory and one or more processors operatively coupled to the memory, the memory and the one or more processors configured to determine an angular motion using at least one gyroscope; and adjust at least one measurement from at least one sensor that is associated with the UE and used to measure relative position, based at least in part on the angular motion.

In some implementations, a non-transitory computer-readable medium storing a set of instructions for wireless communication includes one or more instructions that, when executed by one or more processors of a UE, cause the UE to determine an angular motion using at least one gyroscope of the UE; and adjust at least one measurement from at least one sensor that is associated with the UE and used to measure relative position, based at least in part on the angular motion.

In some implementations, an apparatus for wireless communication includes means for determining an angular motion using at least one gyroscope; and means for adjusting at least one measurement from at least one sensor that is associated with the apparatus and used to measure relative position, based at least in part on the angular motion.

Aspects generally include a method, apparatus, system, computer program product, non-transitory computer-readable medium, user device, user equipment, wireless communication device, and/or processing system as substantially described with reference to and as illustrated by the drawings and specification.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF THE DRAWINGS

So that the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

Figure 1:
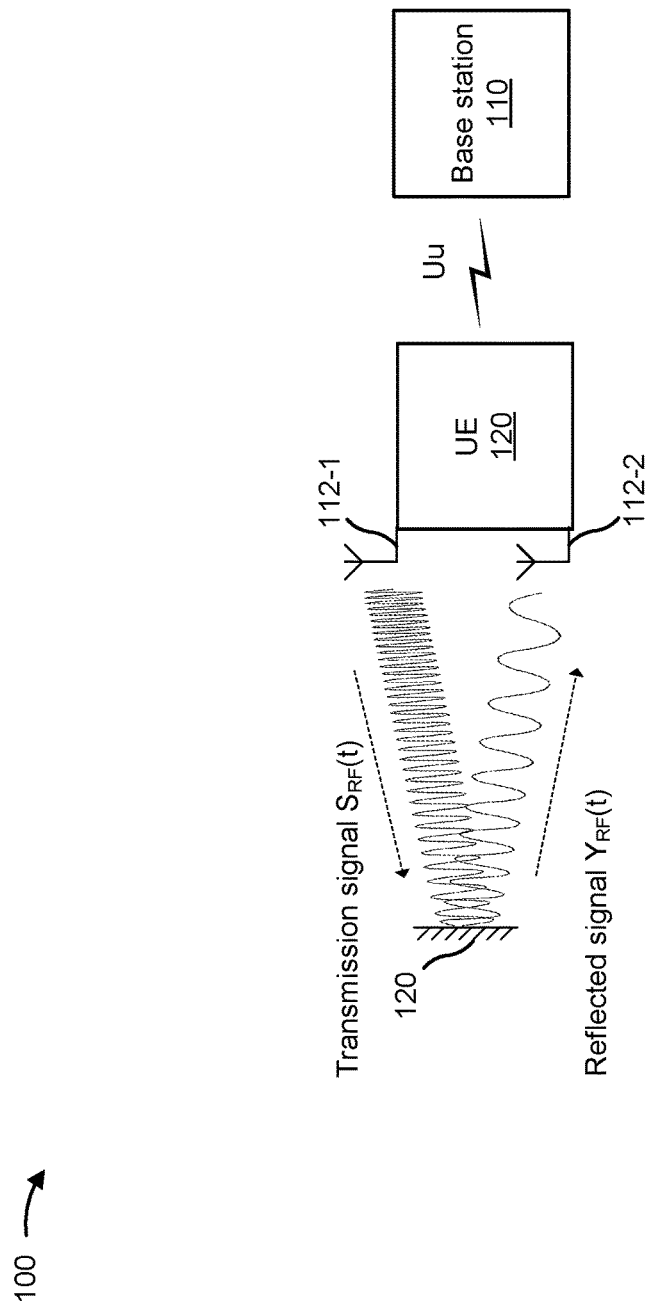
FIG. 1 is a diagram illustrating an example environment in which a UE described herein may be implemented, in accordance with the present disclosure.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

UEs may use one or more technologies to detect and measure nearby objects, such as infrared sensing, radio frequency radar (e.g., FMCW radar and/or other radar techniques), optical detection and classification of objects (e.g., using at least one camera), and/or other similar techniques. Additionally, the UE may classify those objects as animate or inanimate based on measurements of the object. For example, small motions of a nearby object may be indicative of heartbeat patterns, breathing patterns, natural tremors, and/or other signs of animacy. Some technologies, such as FMCW radar, are precise enough to detect as small as 1 mm of motion.

However, a user holding a UE may exhibit one or more small motions. For example, a user's heartbeat may have an amplitude between 0.08 and 0.4 mm, a user's breathing may exhibit an amplitude between 0.8 and 6.0 mm in a front of the user's body and 0.2 mm on a back of the user's body, natural hand tremors may exhibit an amplitude between 0.5 and 2 mm, and other motion of the user's body may similarly disrupt measurements of nearby objects. Accordingly, FMCW radar and other technologies may incorrectly categorize inanimate objects as animate and/or animate objects as inanimate based on errors in measurement caused by the user's motions.

Cameras may adjust for these small motions using electronic image stabilization (EIS) and/or optical image stabilization (OIS). However, EIS relies on sacrificing some pixels that were captured; no similar procedure for sacrificing some measurements would improve the accuracy of FMCW radar or other technologies. OIS relies on physical movements of the camera's lens to compensate for the user's motions. However, antennas used for FMCW and/or other sensors used to detect nearby objects cannot be placed on a mechanical assembly and moved to compensate for the user's motions.

Most UEs include at least one gyroscope (e.g., embedded within an inertial measurement unit (IMU) or other device). Some implementations described herein enable a UE to use measurements from the at least one gyroscope to compensate for angular motion of the UE. As a result, FMCW radar and other technologies may be used to obtain more accurate measurements of nearby objects. Moreover, this may result in more accurate classification of those objects as animate or inanimate. Additionally, in some implementations, the UE may use at least one accelerometer (e.g., embedded within an IMU or other device) to further compensate for linear movement of the UE. As a result, the accuracy of FMCW radar and other technologies may be further increased.

FIG. 1 is a diagram of an example environment 100 in which systems and/or methods described herein may be implemented. As shown in FIG. 1, environment 100 may include a base station 110 and a UE 120. Devices of environment 100 may interconnect via wired connections (e.g., base station 110 may connects to a core via a wired backhaul), wireless connections (e.g., UE 120 may connect to base station 110 via an over-the-air (OTA) interface, such as a Uu interface), or a combination of wired and wireless connections (e.g., base station 110 may connect to the core network via a wireless backhaul in addition to or in lieu of a wired backhaul).

The UE 120 may include a communication device and/or a computing device. For example, the UE 120 may include a wireless communication device, a mobile phone, a user equipment, a laptop computer, a tablet computer, a gaming console, a wearable communication device (e.g., a smart wristwatch, a pair of smart eyeglasses, a head mounted display, or a virtual reality headset), or a similar type of device. As shown in FIG. 1, the UE 120 may further include one or more sensors, such as antennas 112-1 and 112-2. As shown in FIG. 1, antenna 112-1 may transmit a signal (represented by $S_{RF}(t)$ in example 100), which may reflect off one or more external objects (e.g., target 120). The reflection signal (represented by $Y_{RF}(t)$ in example 100) may be detected by antenna 112-2. Accordingly, the UE 120 may use antennas 112-1 and 112-2 to detect and measure nearby objects. In other examples, the UE 120 may use additional antennas (e.g., three antennas or more), fewer antennas (e.g., a single antenna), and/or other sensors (e.g., one or more cameras and/or one or more infrared sensors). In some implementations, the UE 120 may implement a system and/or method for measurement compensation for UE motion, as described elsewhere herein.

Base station 110 may include one or more devices capable of communicating with UE 120 and may also be referred to as a New Radio (NR) base station (BS), a Node B, a gNB, a 5G node B (NB), an access point, a transmit receive point (TRP), or other similar term. Additionally, base station 110 may include one or more devices capable of receiving coordination and control signals from a core network via a backhaul. For example, base station 110 may connect to a telecommunications core network, such as a 5G next generation core network (NG Core), a Long Term Evolution (LTE) evolved packet core (EPC), and/or other similar telecommunications core networks. Base station 110 may provide communication coverage for a particular geographic area. In standards promulgated by the Third Generation Partnership Project (3GPP), the term "cell" can refer to a coverage area of a BS and/or a BS subsystem serving this coverage area, depending on the context in which the term is used.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2A:
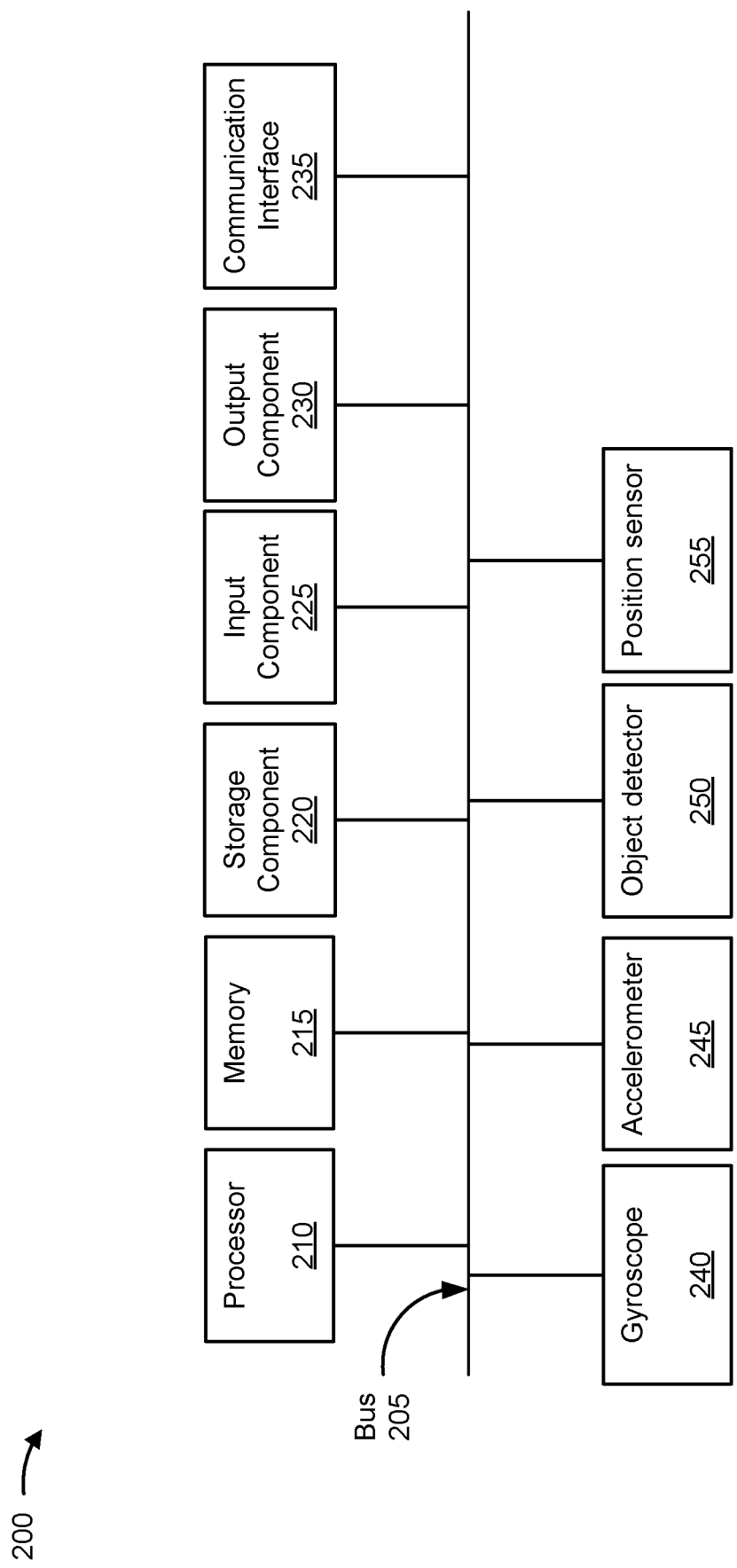
FIG. 2A is a diagram illustrating example components of one or more devices shown in FIG. 1, such as a UE, in accordance with the present disclosure.

FIG. 2A is a diagram illustrating example components of a device 200, in accordance with the present disclosure. Device 200 may correspond to UE 120. In some implementations, UE 120 may include one or more devices 200 and/or one or more components of device 200. As shown in FIG. 2A, device 200 may include a bus 205, a processor 210, a memory 215, a storage component 220, an input component 225, an output component 230, a communication interface 235, a gyroscope 240, an accelerometer 245, an object detector 250, a position sensor 255, and/or the like.

Bus 205 includes a component that permits communication among the components of device 200. Processor 210 is implemented in hardware, firmware, or a combination of hardware and software. Processor 210 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 210 includes one or more processors capable of being programmed to perform a function. Memory 215 includes a random access memory (RAM), a read only memory (ROM), and/or another type of dynamic or static storage device (e.g., a flash memory, a magnetic memory, and/or an optical memory) that stores information and/or instructions for use by processor 210.

Storage component 220 stores information and/or software related to the operation and use of device 200. For example, storage component 220 may include a solid state drive (SSD), a flash memory, a RAM, a ROM and/or another type of non-transitory computer-readable medium.

Input component 225 includes a component that permits device 200 to receive information, such as via user input (e.g., a touch screen display, a keyboard, a keypad, a mouse, a button, a switch, and/or a microphone). Output component 230 includes a component that provides output information from device 200 (e.g., a display, a speaker, a haptic feedback component, an audio or visual indicator, and/or the like).

Communication interface 235 includes a transceiver-like component (e.g., a transceiver and/or a separate receiver and transmitter) that enables device 200 to communicate with other devices, such as via a wired connection, a wireless connection, or a combination of wired and wireless connections. Communication interface 235 may permit device 200 to receive information from another device and/or provide information to another device. For example, communication interface 235 may include an Ethernet interface, an optical interface, a coaxial interface, an infrared interface, a radio frequency interface, a universal serial bus (USB) interface, a wireless local area interface (e.g., a Wi-Fi interface), a cellular network interface, and/or the like.

Gyroscope 240 includes a component that generates one or more measurements related to angular motion of the device 200. In some implementations, the one or more measurements may include an angular velocity, a roll angle, a pitch angle, a yaw angle, and/or another angle (e.g., from a coordinate system centered on the gyroscope 240). For example, gyroscope 240 may include a microelectromechanical systems (MEMS) gyroscope, and/or another type of gyroscope.

Accelerometer 245 includes a component that generates one or more measurements related to linear acceleration of the device 200. In some implementations, the one or more measurements may include proper acceleration (e.g., with respect to a rest frame of accelerometer 245 rather than a fixed coordinate system). For example, accelerometer 245 may include a piezoelectric accelerometer, a surface micromachined capacitive accelerometer, a resonance accelerometer, and/or another type of accelerometer.

Object detector 250 includes a component that detects and measures movement of an object external to device 200. For example, object detector 250 may include an infrared sensor, one or more antennas configured to perform radio frequency radar (e.g., FMCW radar and/or other radar techniques), a camera, and/or another similar sensor.

Position sensor 255 includes a component that determines a position associated with the device 200. In some implementations, position sensor 255 may generate a measurement of absolute position (e.g., using inertial coordinates) associated with the device 200, or of relative position (e.g., with reference to a stationary point, such as a center of Earth or a base station, and/or with reference to a surface, such as a surface of Earth) associated with the device 200. For example, position sensor 255 may include a global navigation satellite system (GNSS) device, a magnetometer, and/or another similar sensor.

Device 200 may perform one or more processes described herein. Device 200 may perform these processes based on processor 210 executing software instructions stored by a non-transitory computer-readable medium, such as memory 215 and/or storage component 220. A computer-readable medium is defined herein as a non-transitory memory device. A memory device includes memory space within a single physical storage device or memory space spread across multiple physical storage devices.

Software instructions may be read into memory 215 and/or storage component 220 from another computer-readable medium or from another device via communication interface 235. When executed, software instructions stored in memory 215 and/or storage component 220 may cause processor 210 to perform one or more processes described herein. Additionally, or alternatively, hardwired circuitry may be used in place of or in combination with software instructions to perform one or more processes described herein. Thus, aspects described herein are not limited to any specific combination of hardware circuitry and software.

In some implementations, device 200 includes means for performing one or more processes described herein and/or means for performing one or more operations of the processes described herein. For example, device 200 may include means for determining an angular motion using at least one gyroscope; and/or means for adjusting at least one measurement from at least one sensor that is associated with the apparatus and used to measure relative position, based at least in part on the angular motion. In some implementations, such means may include one or more components of device 200 described in connection with FIG. 2A, such as bus 205, processor 210, memory 215, storage component 220, input component 225, output component 230, communication interface 235, gyroscope 240, accelerometer 245, object detector 250, position sensor 255, and/or the like.

In some implementations, device 200 may further include means for classifying an external object as animate or inanimate based at least in part on the at least one measurement after adjusting. Additionally, or alternatively, device 200 may further include means for determining at least one distance between the at least one sensor and an estimated grip associated with the device 200. Accordingly, device 200 may further include means for determining at least one translation associated with the at least one sensor based at least in part on the angular motion and the at least one distance.

Additionally, or alternatively, device 200 may include means for determining at least one linear movement of the device 200 using at least one measurement from at least one accelerometer. Additionally, device 200 may include means for receiving at least one relative distance between the at least one sensor and the at least one accelerometer and means for determining at least one translation associated with the at least one sensor based at least in part on the angular motion, the at least one linear movement, and the at least one relative distance.

In some implementations, device 200 may further include means for projecting the at least one translation onto a direction associated with the at least one sensor.

The number and arrangement of components shown in FIG. 2A are provided as an example. In practice, device 200 may include additional components, fewer components, different components, or differently arranged components than those shown in FIG. 2A. Additionally, or alternatively, a set of components (e.g., one or more components) of device 200 may perform one or more functions described as being performed by another set of components of device 200.

Figure 2B:
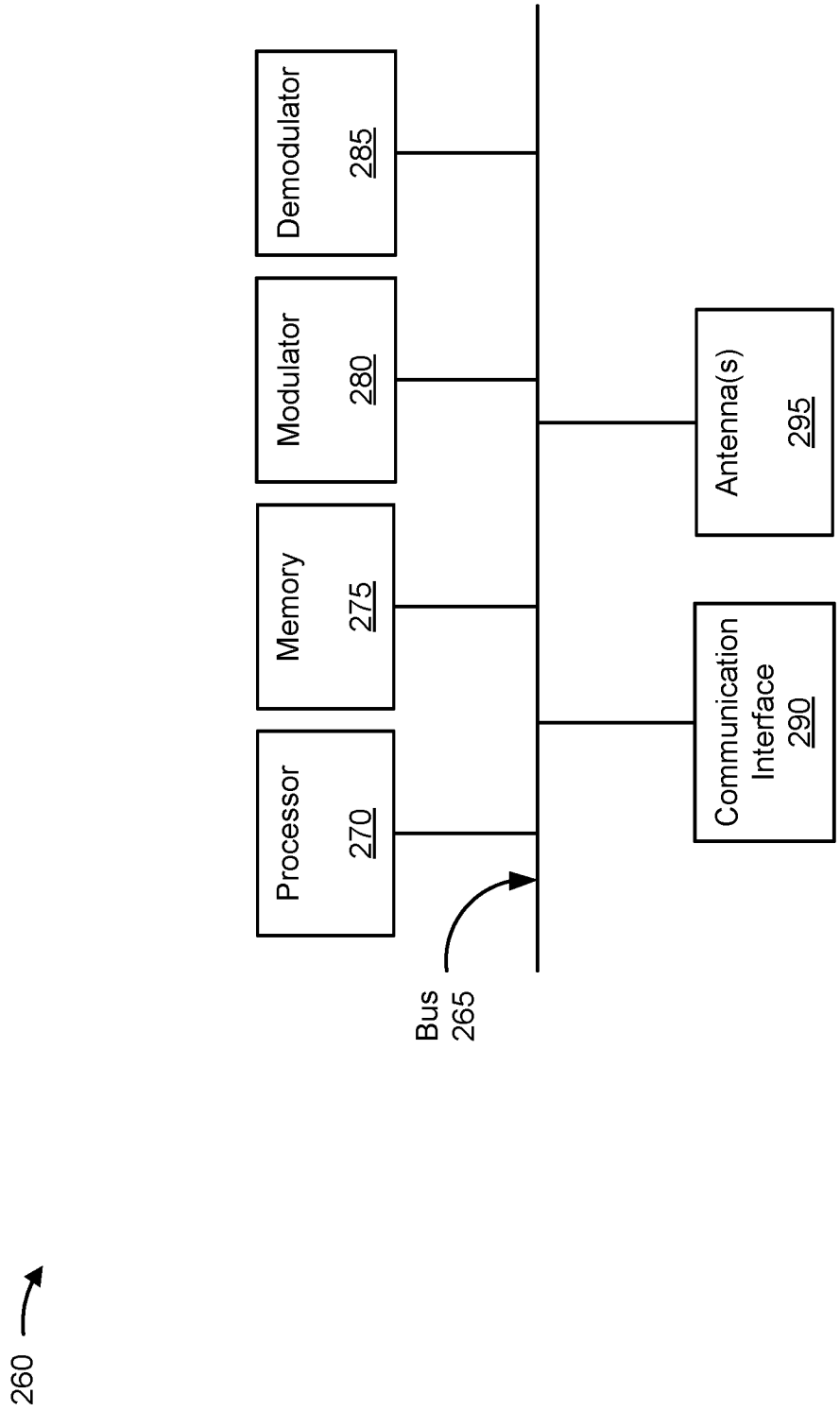
FIG. 2B is a diagram illustrating example components of a frequency-modulated continuous-wave (FMCW) radar device, in accordance with the present disclosure.

FIG. 2B is a diagram illustrating example components of a device 260, in accordance with the present disclosure. Device 260 may be a radar device, such as an FMCW radar device. Device 260 may be included in device 200 of FIG. 2A. Accordingly, in some implementations, UE 120 may include one or more devices 260 and/or one or more components of device 260. As shown in FIG. 2B, device 260 may include a bus 265, a processor 270, a memory 275, a modulator 280, a demodulator 285, a communication interface 290, one or more antennas 295, and/or the like.

Bus 265 includes a component that permits communication among the components of device 260. Processor 270 is implemented in hardware, firmware, or a combination of hardware and software. Processor 210 is a CPU, a GPU, an APU, a microprocessor, a microcontroller, a DSP, a FPGA, an ASIC, or another type of processing component. In some implementations, processor 270 includes one or more processors capable of being programmed to perform a function. For example, processor 270 may transmit signals to modulator 280 and/or antenna(s) 295 that cause transmission of one or more radar signals. Additionally, or alternatively, processor 270 may perform some pre-processing on received signals from demodulator 285 and/or antenna(s) 295 before the pre-processed signals are sent (e.g., via communication interface 290) to another processor (e.g., process 210 of device 200) for further processing. Memory 275 includes a RAM, a ROM, and/or another type of dynamic or static storage device (e.g., a flash memory, a magnetic memory, and/or an optical memory) that stores information and/or instructions for use by processor 270.

Modulator 280 includes a component that generates an analog signal for transmission (e.g., using antenna(s) 295). For example, modulator 280 may encode a digital signal as an electromagnetic signal that can be transmitted over-the-air (e.g., by antenna(s) 295). Similarly, demodulator 285 includes a component that generates a digital signal for processing based at least in part on an analog signal (e.g., received using antenna(s) 295). For example, demodulator 285 may decode a digital signal based at least in part on an electromagnetic signal that was received (e.g., by antenna(s) 295). In some implementations, device 260 may function as a continuous wave radar (e.g., an FMCW radar) such that processor 270 and/or modulator 280 causes antenna(s) 295 to transmit a continuous radio wave with a stable frequency, and demodulator 285 and/or processor 270 filters analog signals, from the antenna(s) 295, based at least in part on the stable frequency, such that objects near device 260 can be detected using the Doppler effect.

Communication interface 290 includes a transceiver-like component (e.g., a transceiver and/or a separate receiver and transmitter) that enables device 200 to communicate with other devices, such as via a wired connection, a wireless connection, or a combination of wired and wireless connections. Communication interface 290 may permit device 200 to receive information from another device and/or provide information to another device. For example, communication interface 295 may include an Ethernet interface, an optical interface, a coaxial interface, an infrared interface, a radio frequency interface, a USB interface, a wireless local area interface (e.g., a Wi-Fi interface), a cellular network interface, and/or the like.

Antenna(s) 295 includes one or more antenna elements that transmit electromagnetic signals based at least in part on analog signals and/or generate analog signals based at least in part on received electromagnetic signals. In some implementations, antenna(s) 295 may include, or may be included within, one or more antenna panels, antenna groups, sets of antenna elements, and/or antenna arrays, among other examples. An antenna panel, an antenna group, a set of antenna elements, and/or an antenna array may include one or more antenna elements. An antenna panel, an antenna group, a set of antenna elements, and/or an antenna array may include a set of coplanar antenna elements and/or a set of non-coplanar antenna elements. An antenna panel, an antenna group, a set of antenna elements, and/or an antenna array may include antenna elements within a single housing and/or antenna elements within multiple housings.

Device 260 may perform one or more processes described herein. Device 260 may perform these processes based on processor 270 executing software instructions stored by a non-transitory computer-readable medium, such as memory 275. A computer-readable medium is defined herein as a non-transitory memory device. A memory device includes memory space within a single physical storage device or memory space spread across multiple physical storage devices.

Software instructions may be read into memory 275 from another computer-readable medium or from another device via communication interface 290. When executed, software instructions stored in memory 275 may cause processor 270 to perform one or more processes described herein. Additionally, or alternatively, hardwired circuitry may be used in place of or in combination with software instructions to perform one or more processes described herein. Thus, aspects described herein are not limited to any specific combination of hardware circuitry and software.

In some implementations, device 260 includes means for performing one or more processes described herein and/or means for performing one or more operations of the processes described herein. For example, device 260 may include means for adjusting at least one measurement from the device 260. In some implementations, such means may include one or more components of device 270 described in connection with FIG. 2B, such as bus 265, processor 270, memory 275, modulator 280, demodulator 285, communication interface 290, antenna(s) 295, and/or the like. In some implementations, device 260 may further include means for classifying an external object as animate or inanimate based at least in part on the at least one measurement after adjusting.

The number and arrangement of components shown in FIG. 2B are provided as an example. In practice, device 260 may include additional components, fewer components, different components, or differently arranged components than those shown in FIG. 2B. Additionally, or alternatively, a set of components (e.g., one or more components) of device 260 may perform one or more functions described as being performed by another set of components of device 260.

Figure 3A:
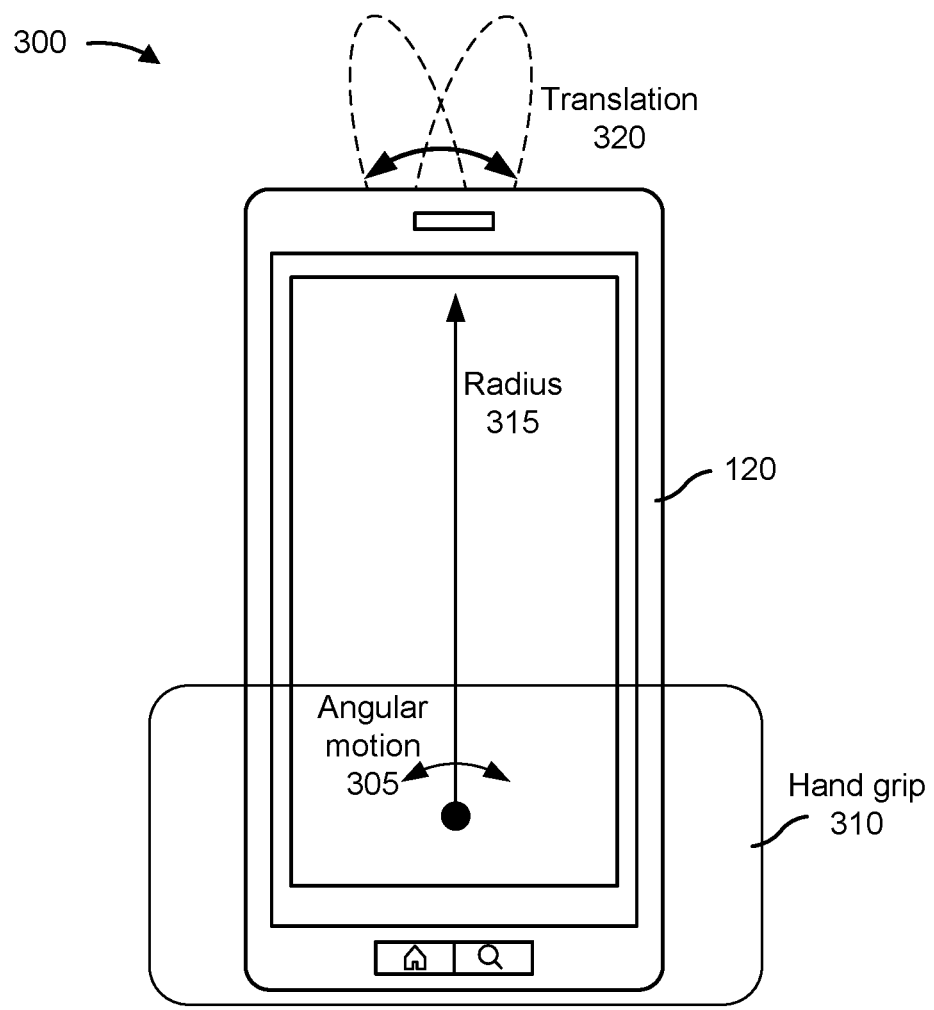
FIGS. 3A and 3B are diagrams illustrating examples associated with measurement compensation for UE motion, in accordance with the present disclosure.

FIG. 3A is a diagram illustrating an example 300 associated with measurement compensation for UE motion, in accordance with the present disclosure. As shown in FIG. 3A, example 300 includes a UE 120. In some implementations, the UE 120 may include at least one gyroscope. For example, the UE 120 may include at least one inertial measurement unit (IMU) that includes the at least one gyroscope and/or may include at least one standalone gyroscope.

The UE 120 may determine an angular motion 305 using the at least one gyroscope. For example, the at least one gyroscope may output an angular velocity such that the UE 120 may determine an angular motion associated with the UE 120 by computing an angle from the at least one gyroscope. For example, the UE 120 may use a gyro quaternion or rotation matrix (e.g., along with tilt correction and/or other corrections) to determine the angular motion 305. In some implementations, the angular motion may be defined by an amplitude and a phase of angular vibration of the UE 120. The amplitude and phase may depend on motion associated with the UE 120, such as motion caused by a user's heartbeat, breathing, hand tremors, and/or other similar action.

The UE 120 may adjust at least one measurement from at least one sensor that is associated with the UE 120 and used to measure relative position, based at least in part on the angular motion 305. In some implementations, the at least one sensor may include an infrared sensor, one or more antennas configured to perform radio frequency radar (e.g., FMCW radar and/or other radar techniques), a camera, and/or another similar sensor used to detect and measure relative position of an external object. Accordingly, the UE 120 may adjust at least one measurement based at least in part on the angular motion 305 by increasing or decreasing one or more measurements from an infrared sensor to account for angular motion 305 of the UE 120, by increasing or decreasing one or more measurements of reflected signals from a radar to account for angular motion 305 of the UE 120, by mapping pixels from one measurement of a camera to pixels of another measurement from the camera to account for angular motion 305 of the UE 120, and/or otherwise accounting for the angular motion 305.

In some implementations, the UE 120 may further determine at least one distance between the at least one sensor and an estimated grip (e.g., hand grip 310 in example 300) associated with the UE 120. In some aspects, the UE 120 may estimate the hand grip 310 based at least in part on measurements from the at least one gyroscope, an accelerometer, an ambient light sensor, and/or another sensor of the UE 120. For example, as described below in connection with FIG. 7, the UE 120 may estimate an orientation of the UE 120 and estimate an axis based at least in part on the orientation. In some aspects, and as described below in connection with FIG. 7, the UE 120 may further estimate the hand grip 310 and estimate the axis based at least in part on the hand grip 310. Additionally, or alternatively, and as described below in connection with FIG. 7, the UE 120 may further estimate one or more grip points associated with the hand grip 310 and estimate the axis based at least in part on the one or more grip points. The at least one distance may comprise a radius 315 between the axis that is associated with the angular motion and determined based at least in part on hand grip 310 and a location that is associated with the at least one sensor. The axis may be in a volume of the UE 120, as shown in FIG. 3A, or may be outside the volume. The UE 120 may receive the location associated with the at least one sensor from a storage (e.g., the location may be stored on a chipset of the UE 120 by an original equipment manufacturer (OEM) or an operating system (OS) developer) or may determine the location associated with the at least one sensor (e.g., based on measurements of electric signals transmitted to and received from the at least one sensor by another component of the UE 120).

Accordingly, the UE 120 may determine at least one translation 320 associated with the at least one sensor based at least in part on the angular motion and the at least one distance. For example, the UE 120 may combine (e.g., multiply) at least a portion of the angular motion (e.g., a portion of the angular motion 405 projected along an axis associated with the radius 315, as described below) with the radius 315 to determine the at least one translation 320.

In some implementations, the UE 120 may adjust the at least one measurement by offsetting the at least one measurement based at least in part on the at least one translation 320. For example, the UE 120 may increase or decrease the at least one measurement, as described above. In some implementations, the UE 120 may project the at least one translation 320 onto a direction associated with the at least one sensor such that the at least one measurement is adjusted based at least in part on the projection. For example, the UE 120 may discard a component of the angular motion along an axis parallel to the radius 315 and use a component of the angular motion along an axis perpendicular to the radius 315 to determine the at least one translation 320.

In some implementations, the at least one sensor may include a plurality of sensors (e.g., two or more antennas, at least one antenna in combination with an infrared sensor and/or camera, and/or another combination of two or more sensors). Accordingly, the UE 120 may determine a corresponding plurality of distances (e.g., a corresponding plurality of radii) and thus determine a corresponding plurality of translations associated with those sensors. For example, the UE 120 may project the angular motion onto different axes for each sensor in order to calculate the corresponding plurality of translations. The UE 120 may further adjust one or more measurements from each sensor based on the corresponding translation for that sensor.

As described above, the at least one sensor may be used to measure relative position with respect to an external object that is to be classified as animate or inanimate. Accordingly, the UE 120 may classify the external object as animate or inanimate based at least in part on the at least one measurement after adjusting. For example, if the at least one measurement before adjusting was indicative of animacy (e.g., by satisfying an animacy threshold and/or one or more other animacy conditions), the at least one measurement after adjusting may no longer be indicative of animacy. Similarly, if the at least one measurement before adjusting was indicative of inanimacy (e.g., by satisfying an inanimacy threshold and/or one or more other inanimacy conditions), the at least one measurement after adjusting may no longer be indicative of inanimacy.

By using techniques as described in connection with FIG. 3A, the UE 120 may compensate for angular motion of the UE 120 when detecting and measuring an external object. As a result, FMCW radar and other technologies may be used to obtain more accurate measurements of nearby objects. Moreover, the UE 120 may more accurately classify the external object as animate or inanimate based on the measurements.

As indicated above, FIG. 3A is provided as an example. Other examples may differ from what is described with respect to FIG. 3A.

Figure 3B:
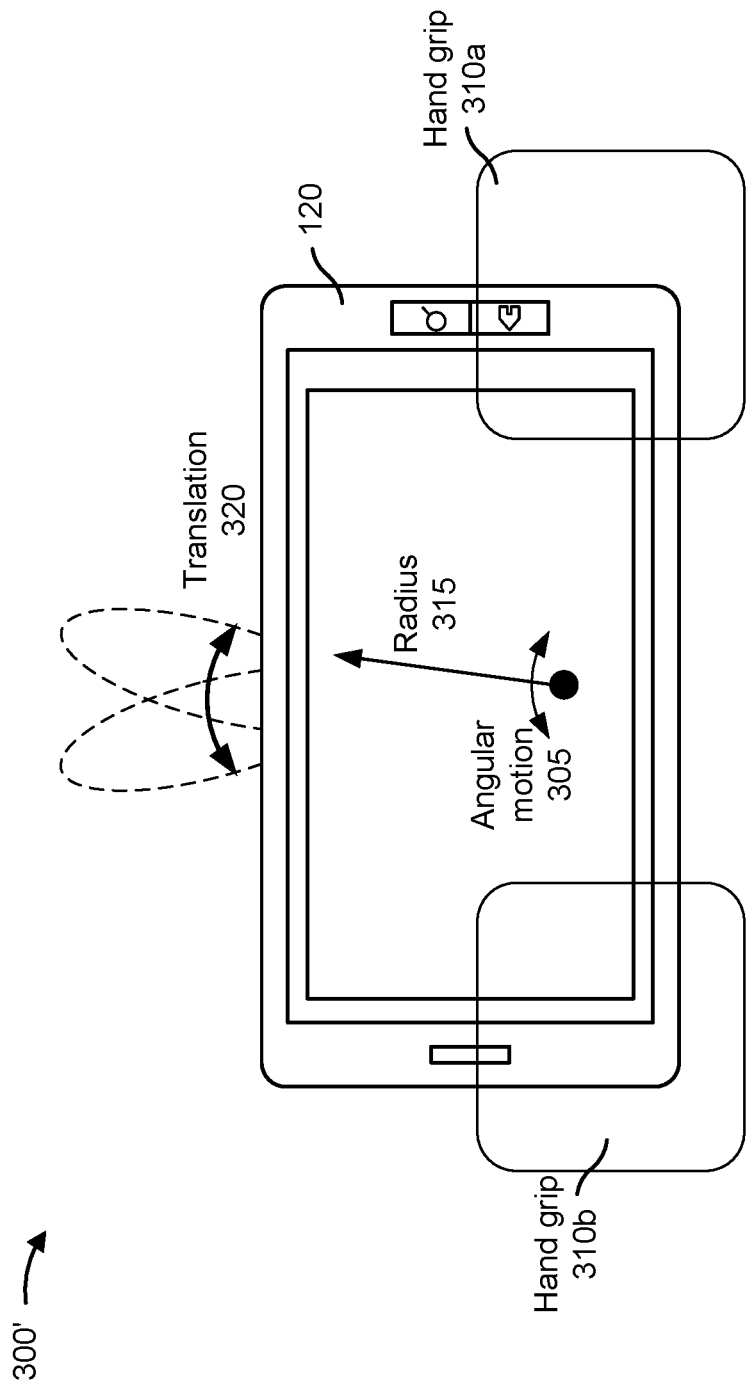

FIG. 3B is a diagram illustrating another example 300' associated with measurement compensation for UE motion, in accordance with the present disclosure. Example 300' is similar to example 300 and includes a UE 120 with at least one gyroscope. For example, the UE 120 may include at least one IMU that includes the at least one gyroscope and/or may include at least one standalone gyroscope.

In example 300', the UE 120 may determine an angular motion 305 using the at least one gyroscope and adjust at least one measurement from at least one sensor that is associated with the UE 120 and used to measure relative position, based at least in part on the angular motion 305, as described above in connection with FIG. 3A.

Additionally, in some implementations and as described above in connection with FIG. 3A, the UE 120 may further determine at least one distance between the at least one sensor and estimated grips (e.g., hand grips 310a and 310b in example 300') associated with the UE 120. The at least one distance may comprise a radius 315 between an axis that is associated with the angular motion and determined based at least in part on hand grips 310a and 310b and a location that is associated with the at least one sensor.

Furthermore, as described above in connection with FIG. 3A, the UE 120 may determine at least one translation 320 associated with the at least one sensor based at least in part on the angular motion and the at least one distance, and may adjust the at least one measurement by offsetting the at least one measurement based at least in part on the at least one translation 320. Accordingly, similar to example 300, the UE 120 in example 300' may classify an external object as animate or inanimate based at least in part on the at least one measurement after adjusting.

As indicated above, FIG. 3B is provided as an example. Other examples may differ from what is described with respect to FIG. 3B.

Figure 4:
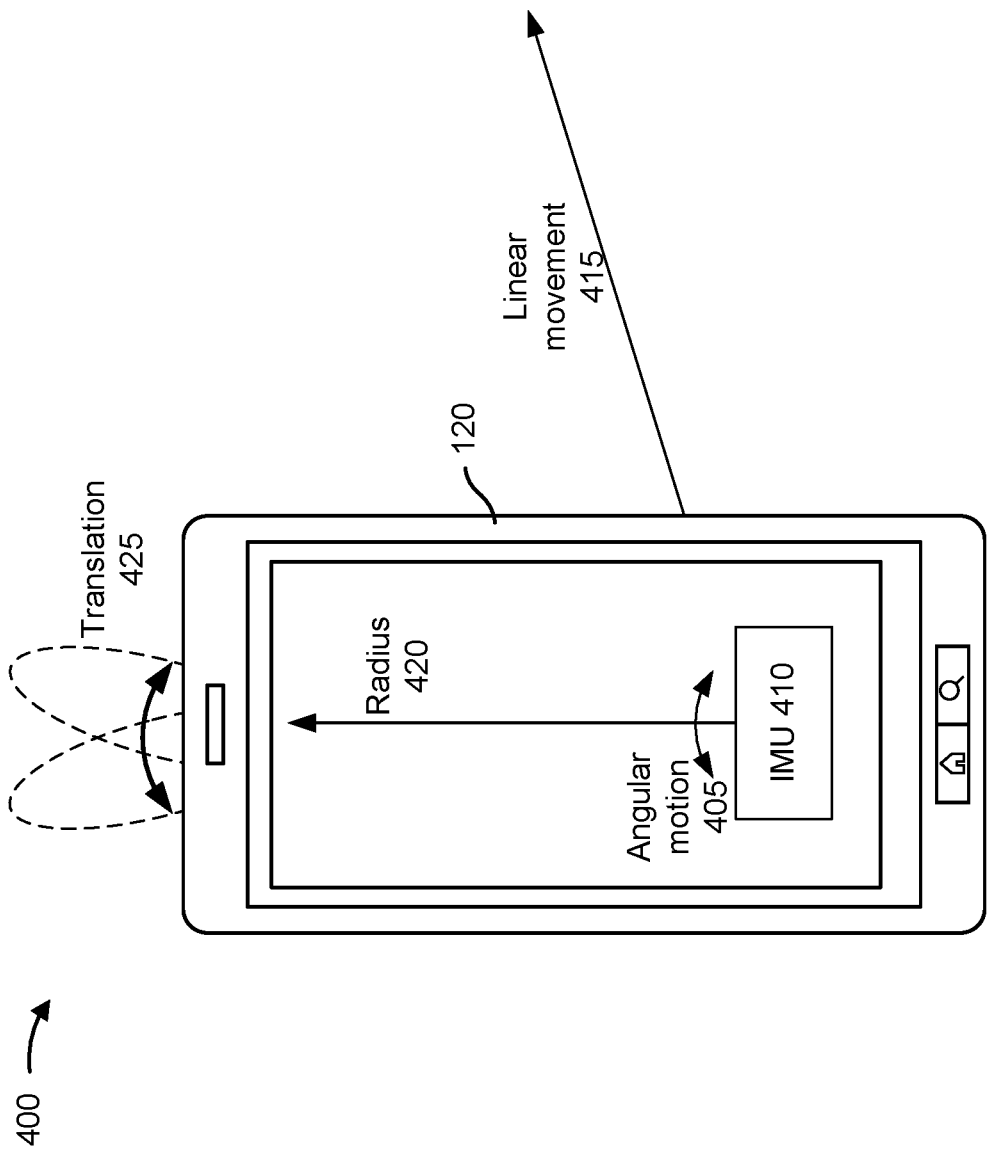
FIG. 4 is a diagram illustrating another example associated with measurement compensation for UE motion, in accordance with the present disclosure.

FIG. 4 is a diagram illustrating another example 400 associated with measurement compensation for UE motion, in accordance with the present disclosure. As shown in FIG. 4, example 400 includes a UE 120. In some implementations, the UE 120 may include at least one gyroscope and at least one accelerometer. For example, the UE 120 may include at least one IMU 410 that includes the at least one gyroscope and/or the at least one accelerometer. Additionally, or alternatively, the UE 120 may include at least one standalone gyroscope and/or at least one standalone accelerometer.

The UE 120 may determine an angular motion 305 using the at least one gyroscope. For example, the at least one gyroscope may output an angular velocity such that the UE 120 may determine an angular motion associated with the UE 120 by computing an angle from the at least one gyroscope. For example, the UE 120 may use a gyro quaternion or rotation matrix (e.g., along with tilt correction and/or other corrections) to determine the angular motion 405. In some implementations, the angular motion may be defined by an amplitude and a phase of angular vibration of the UE 120. The amplitude and phase may depend on motion associated with the UE 120, such as motion caused by a user's heartbeat, breathing, hand tremors, and/or other similar action. As described above in connection with FIG. 3A, the UE 120 may adjust at least one measurement from at least one sensor that is associated with the UE 120 and used to measure relative position, based at least in part on the angular motion 405.

In some implementations, the UE 120 may further determine at least one linear movement of the UE 120 using at least one measurement from the at least one accelerometer. For example, the at least one linear movement may include a linear movement 415 associated with the UE 120. In some implementations, the at least one linear movement may be defined by an amplitude and a phase associated with motion of the UE 120. The amplitude and phase may depend on motion associated with the UE 120, such as motion caused by a user's walking, running, driving, and/or other similar action. In some implementations, the UE 120 may adjust the at least one measurement from the at least one accelerometer based at least in part on the angular motion and determine the at least one linear movement using the at least one adjusted measurement. For example, the UE 120 may determine the at least one linear movement as described below in connection with FIG. 5.

Accordingly, the UE 120 may additionally or alternatively adjust the at least one measurement from the at least one sensor, based at least in part on the linear movement 415. In some implementations, the at least one sensor may include an infrared sensor, one or more antennas configured to perform radio frequency radar (e.g., FMCW radar and/or other radar techniques), a camera, and/or another similar sensor used to detect and measure relative position of an external object. Accordingly, the UE 120 may adjust at least one measurement based at least in part on the linear movement 415 by increasing or decreasing one or more measurements from an infrared sensor to account for linear movement 415, by increasing or decreasing one or more measurements of reflected signals from a radar to account for linear movement 415, by mapping pixels from one measurement of a camera to pixels of another measurement from the camera to account for linear movement 415, and/or otherwise accounting for the linear movement 415.

In some implementations, the UE 120 may further receive at least one relative distance between the at least one sensor and the at least one accelerometer. The at least one distance may comprise a radius 420 between a location that is associated with the at least one accelerometer (e.g., included in IMU 410 in example 400) and a location that is associated with the at least one sensor. The UE 120 may receive the at least one relative distance from a storage (e.g., the location may be stored on a chipset of the UE 120 by an OEM or an OS developer) or may determine the at least one relative distance based at least in part on the location associated with the at least one accelerometer (e.g., stored in a storage of the UE 120 or determined based on measurements of electric signals transmitted to and received from the at least one accelerometer by another component of the UE 120) and the location associated with the at least one sensor (e.g., stored in a storage of the UE 120 or determined based on measurements of electric signals transmitted to and received from the at least one sensor by another component of the UE 120).

Accordingly, the UE 120 may determine at least one translation associated with the at least one sensor (e.g., translation 425 in example 400) based at least in part on the angular motion 405, the at least one linear movement (e.g., linear movement 415 in example 400), and the at least one relative distance (e.g., radius 420 in example 400). For example, the UE 120 may calculate a combination (e.g., multiplication) of at least a portion of the angular motion (e.g., a portion of the angular motion 405 projected along an axis associated with the radius 420, as described below) with the radius 420, and further combine (e.g., add) that calculation with the at least one linear movement (e.g., linear movement 415) to determine the at least one translation 425. Accordingly, the at least one translation 425 of the IMU 410 may include a vector sum of the linear movement 415 of the UE 120 with a translation based at least in part on the angular motion 405.

In some implementations, the UE 120 may additionally or alternatively adjust the at least one measurement by offsetting the at least one measurement based at least in part on the at least one translation 425. For example, the UE 120 may increase or decrease the at least one measurement, as described above. In some implementations, the UE 120 may project the at least one translation 425 onto a direction associated with the at least one sensor such that the at least one measurement is adjusted based at least in part on the projection. For example, the UE 120 may discard a component of the angular motion along an axis parallel to the radius 420 and use a component of the angular motion along an axis perpendicular to the radius 420 to determine the at least one translation 425 (e.g., as described above).

As described above, the at least one sensor may be used to measure relative position with respect to an external object that is to be classified as animate or inanimate. Accordingly, the UE 120 may classify the external object as animate or inanimate based at least in part on the at least one measurement after adjusting. For example, if the at least one measurement before adjusting was indicative of animacy (e.g., by satisfying an animacy threshold and/or one or more other animacy conditions), the at least one measurement after adjusting may no longer be indicative of animacy. Similarly, if the at least one measurement before adjusting was indicative of inanimacy (e.g., by satisfying an inanimacy threshold and/or one or more other inanimacy conditions), the at least one measurement after adjusting may no longer be indicative of inanimacy.

By using techniques as described in connection with FIG. 4, the UE 120 may compensate for linear movement of the UE 120 when detecting and measuring an external object. As a result, FMCW radar and other technologies may be used to obtain more accurate measurements of nearby objects. Moreover, the UE 120 may more accurately classify the external object as animate or inanimate based on the measurements.

Example 400 may be combined with examples 300 and/or 300'. In some implementations, the UE 120 may determine at least one translation associated with the at least one sensor based at least in part on an estimated grip associated with the UE 120 (e.g., as described above in connection with FIGS. 3A-3B) and determine at least one translation associated with the at least one sensor based at least in part on the at least one relative distance between the at least one sensor and at least one accelerometer (e.g., as described above in connection with FIG. 4). Accordingly, the UE 120 may adjust the at least one measurement by offsetting the at least one measurement based at least in part on both translations. For example, the UE 120 may combine (e.g., add) both translations and adjust the at least one measurement accordingly.

As indicated above, FIG. 4 is provided as an example. Other examples may differ from what is described with respect to FIG. 4.

Figure 5:
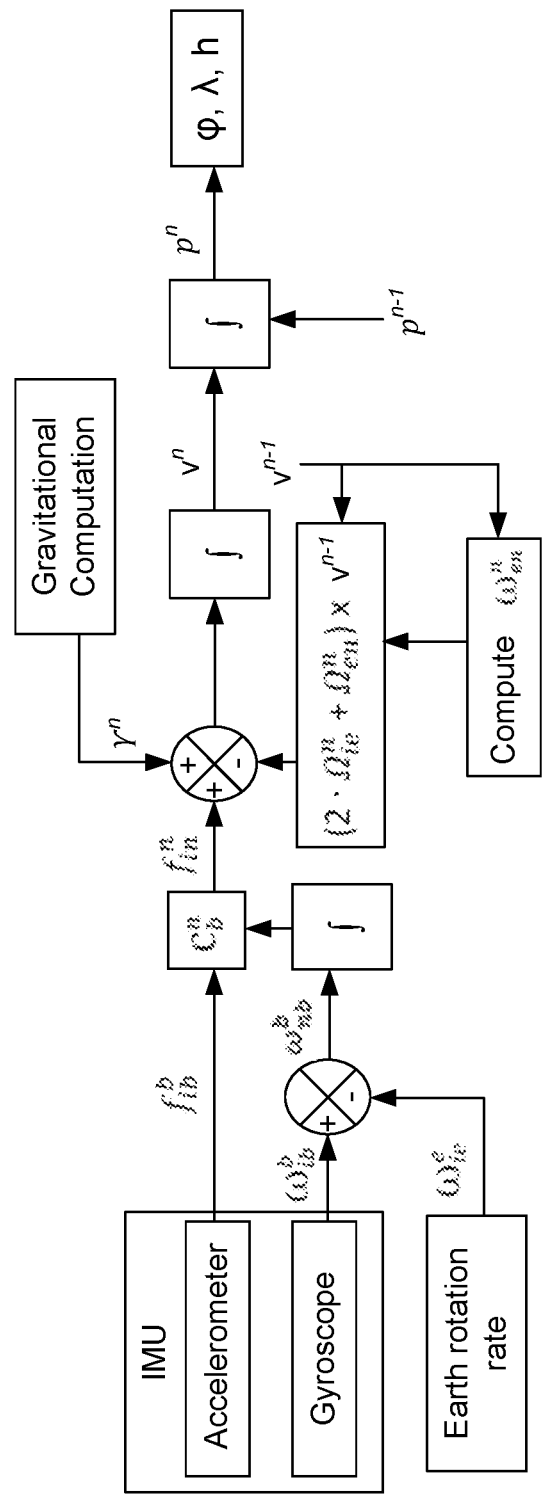
FIG. 5 is a diagram illustrating an example associated with determining linear translation from gyroscope and accelerometer measurements, in accordance with the present disclosure.

FIG. 5 is a diagram illustrating an example 500 associated with determining linear translation from gyroscope and accelerometer measurements, in accordance with the present disclosure. As shown in FIG. 5, a UE (e.g., UE 120) in example 500 may use measurements from at least one accelerometer of an IMU and measurements from at least one gyroscope of an IMU. Additionally, or alternatively, the UE 120 in example 500 may use measurements from at least one standalone accelerometer and/or measurements from at least one standalone gyroscope.

As shown in FIG. 5, angular velocity of the at least one IMU (or body) b and coordinatized with respect to an inertial frame i (represented as $\omega_{ib}^b$ in FIG. 5) is measured by the at least one gyroscope. This angular velocity may be corrected (e.g., via tensor multiplication) to account for Earth's rotation (represented as $\omega_{ie}^e$ in FIG. 5, which is the angular velocity of the Earth e and coordinatized with respect to inertial frame i) to obtain angular velocity of the at least one IMU coordinatized with respect to a navigational frame n (represented as $\omega_{nb}^b$ in FIG. 5).

As further shown in FIG. 5, acceleration of the at least one IMU (or body) b and coordinated with respect to an inertial frame i (represented as $f_{ib}^b$ in FIG. 5) is measured by the at least one accelerometer. This acceleration may be adjusted (e.g., via multiplication) based on an attitude of the body b with respect to the navigational frame n (represented as $C_b^n$ in FIG. 5) to obtain acceleration of the navigational frame n with respect to the inertial frame i (represented as $f_{in}^n$ in FIG. 5). The specific force may be determined from an integration of the angular velocity of the at least one IMU coordinatized with respect to a navigational frame n (e.g., using a gyro quaternion or rotation matrix). A previous velocity of the at least one IMU (represented as $v^{n-1}$ in FIG. 5) may be used to obtain a previous angular velocity of the navigational frame n with respect to Earth e (represented as $\omega_{en}^n$ in FIG. 5). The previous velocity may be adjusted for the Coriolis effect (e.g., by crossing the previous velocity $v^{n-1}$ with $2\cdot\Omega_{ie}^n \cdot \Omega_{en}^n$ in FIG. 5, where $\Omega_{en}^n$ represents the angular velocity of the navigational frame n with respect to Earth e and $\Omega_{ie}^n$ represents the angular velocity of the Earth e with respect to the inertial frame i). Accordingly, the acceleration of the navigational frame n (represented as $f_{in}^n$ in FIG. 5), adjusted previous velocity, and gravitational vector (represented as $Y^n$ in FIG. 5) may be combined using numerical integration to determine a current velocity of the at least one IMU (represented as $v^n$ in FIG. 5). Moreover, the current velocity may be numerically integrated and combined with a previous position of the IMU (represented as $p^{n-1}$ in FIG. 5) to determine a current position of the IMU (represented as $p^n$ in FIG. 5). For example, the current position may be in curvilinear coordinates and thus represented as $\varphi$, $\lambda$, and h in FIG. 5.

As indicated above, FIG. 5 is provided as an example. Other examples may differ from what is described with respect to FIG. 5.

Figure 6:
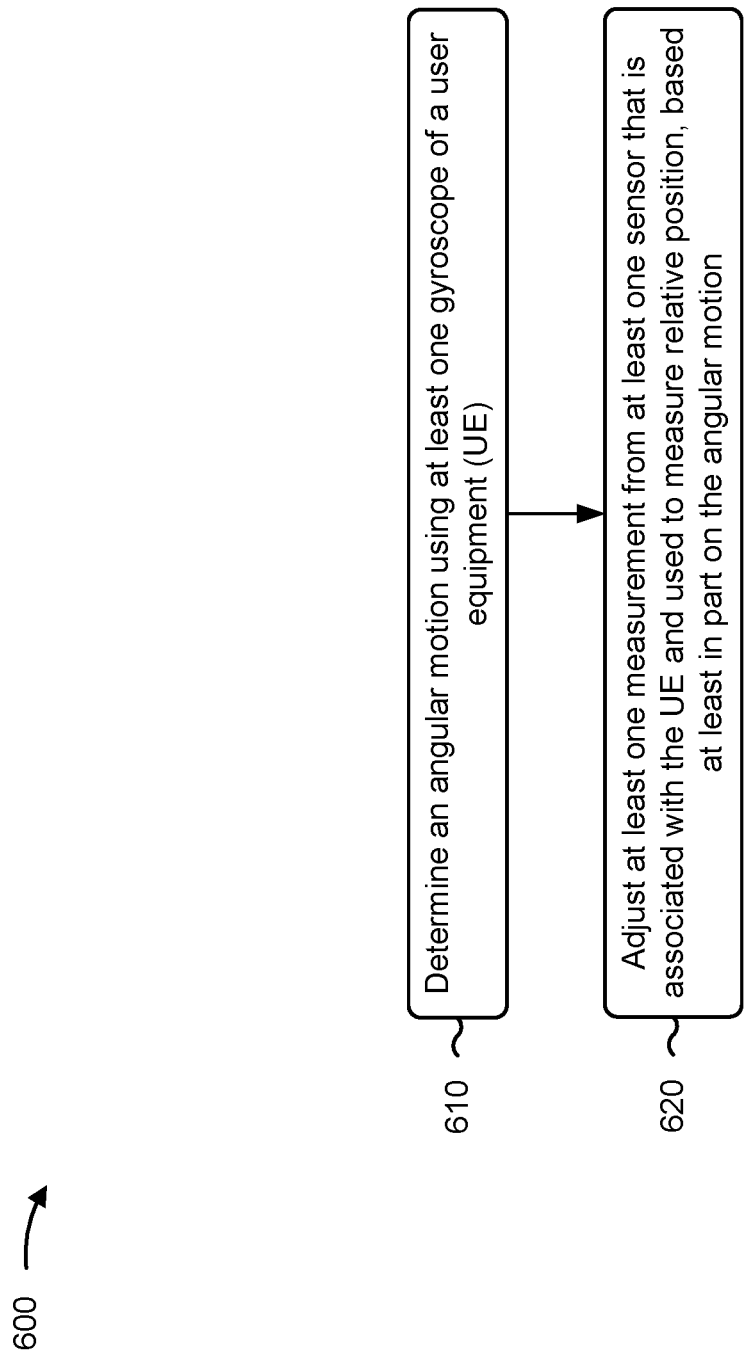
FIG. 6 is a flowchart of an example process associated with measurement compensation for UE motion, in accordance with the present disclosure.

FIG. 6 is a flowchart of an example process 600 associated with angular and linear movement detection and compensation. In some implementations, one or more process blocks of FIG. 6 may be performed by a UE (e.g., UE 120). In some implementations, one or more process blocks of FIG. 6 may be performed by another device or a group of devices separate from or including the UE, such as a gyroscope (e.g., gyroscope 240), an accelerometer (e.g., accelerometer 245), an object detector (e.g., object detector 250), and/or a position sensor (e.g., position sensor 255). Additionally, or alternatively, one or more process blocks of FIG. 6 may be performed by one or more components of device 200, such as bus 205, processor 210, memory 215, storage component 220, input component 225, output component 230, and/or communication interface 235.

As shown in FIG. 6, process 600 may include determining an angular motion of the UE (block 610). For example, the UE may determine an angular motion using at least one gyroscope (e.g., gyroscope 240), as described above.

As further shown in FIG. 6, process 600 may include adjusting at least one measurement from at least one sensor that is associated with the UE and used to measure relative position, based at least in part on the angular motion (block 620). For example, the UE may adjust (e.g., using processor 210) the at least one measurement from the at least one sensor based at least in part on the angular motion, as described above.

Process 600 may include additional implementations, such as any single implementation or any combination of implementations described below and/or in connection with one or more other processes described elsewhere herein.

In a first implementation, the relative position is with respect to an external object to be classified as animate or inanimate.

In a second implementation, alone or in combination with the first implementation, process 600 further includes classifying (e.g., using processor 210) the external object as animate or inanimate based at least in part on the at least one measurement after adjusting.

In a third implementation, alone or in combination with one or more of the first and second implementations, the at least one gyroscope is included in at least one IMU of the UE.

In a fourth implementation, alone or in combination with one or more of the first through third implementations, determining the angular motion includes computing an angle from the at least one gyroscope of the UE.

In a fifth implementation, alone or in combination with one or more of the first through fourth implementations, the angular motion is defined by an amplitude and a phase of angular vibration of the UE.

In a sixth implementation, alone or in combination with one or more of the first through fifth implementations, process 600 further includes determining (e.g., using processor 210) at least one distance between the at least one sensor and an estimated grip associated with the UE.

In a seventh implementation, alone or in combination with one or more of the first through sixth implementations, process 600 further includes determining (e.g., using processor 210) at least one translation associated with the at least one sensor based at least in part on the angular motion and the at least one distance.

In an eighth implementation, alone or in combination with one or more of the first through seventh implementations, adjusting the at least one measurement includes offsetting the at least one measurement based at least in part on the at least one translation.

In a ninth implementation, alone or in combination with one or more of the first through eighth implementations, process 600 further includes projecting (e.g., using processor 210) the at least one translation onto a direction associated with the at least one sensor, and the at least one measurement is adjusted based at least in part on the projection.

In a tenth implementation, alone or in combination with one or more of the first through ninth implementations, process 600 further includes determining (e.g., using processor 210) at least one linear movement of the UE using at least one measurement from at least one accelerometer of the UE, and the at least one measurement from the at least one sensor is adjusted based at least in part on at least one translation associated with the at least one sensor determined from the angular motion and the at least one linear movement.

In an eleventh implementation, alone or in combination with one or more of the first through tenth implementations, the at least one accelerometer is included in at least one IMU of the UE.

In a twelfth implementation, alone or in combination with one or more of the first through eleventh implementations, determining the at least one linear movement includes adjusting the at least one measurement from the at least one accelerometer based at least in part on the angular motion and determining the at least one linear movement using the at least one adjusted measurement.

In a thirteenth implementation, alone or in combination with one or more of the first through twelfth implementations, the at least one linear movement is defined by an amplitude and a phase associated with motion of the UE.

In a fourteenth implementation, alone or in combination with one or more of the first through thirteenth implementations, process 600 further includes receiving (e.g., using memory 215, storage component 220, and/or input component 225) at least one relative distance between the at least one sensor and the at least one accelerometer.

In a fifteenth implementation, alone or in combination with one or more of the first through fourteenth implementations, process 600 further includes determining (e.g., using processor 210) at least one translation associated with the at least one sensor based at least in part on the angular motion, the at least one linear movement, and the at least one relative distance.

In a sixteenth implementation, alone or in combination with one or more of the first through fifteenth implementations, process 600 further includes projecting (e.g., using processor 210) the at least one translation onto a direction associated with the at least one sensor, wherein the at least one measurement is adjusted based at least in part on the projection.

In a seventeenth implementation, alone or in combination with one or more of the first through sixteenth implementations, the at least one sensor includes a radar device, and adjusting the at least one measurement includes adjusting a signal from the radar device.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
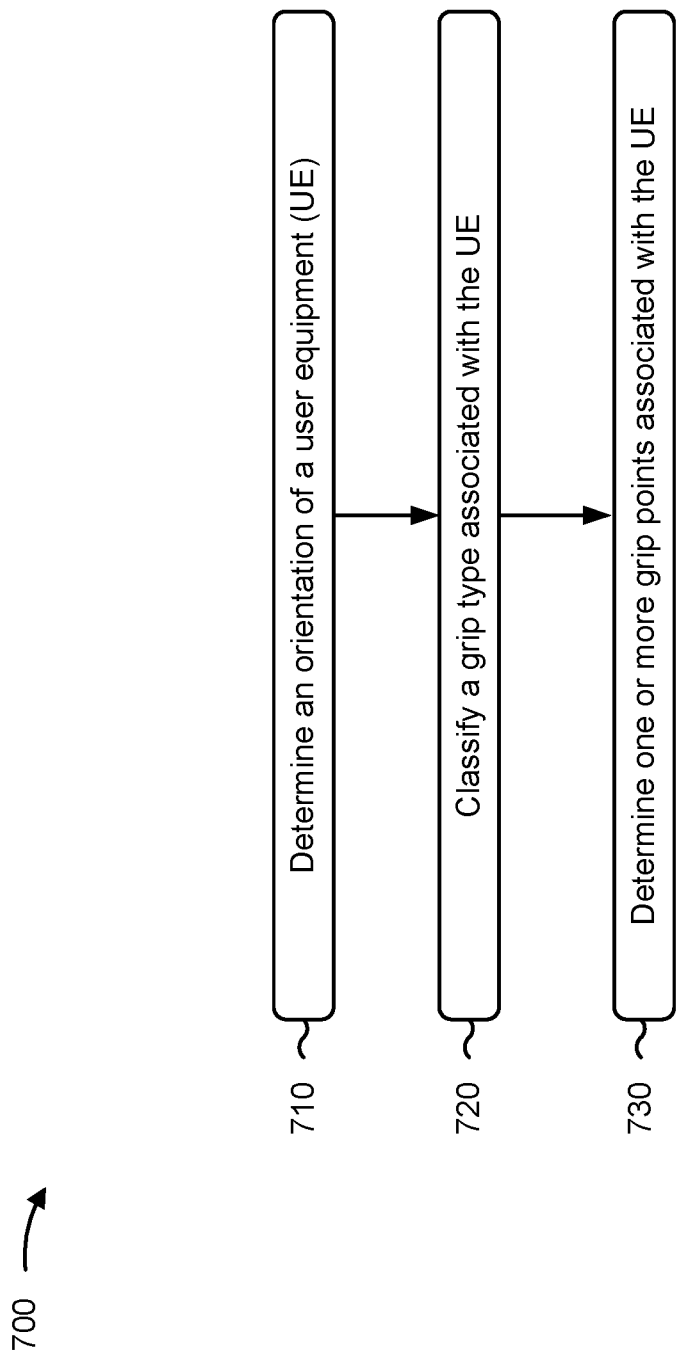
FIG. 7 is a flowchart of an example process associated with estimating a hand grip of a UE, in accordance with the present disclosure.

FIG. 7 is a flowchart of an example process 700 associated with hand grip determination. In some implementations, one or more process blocks of FIG. 7 may be performed by a UE (e.g., UE 120). In some implementations, one or more process blocks of FIG. 7 may be performed by one or more components of device 200, such as bus 205, processor 210, memory 215, storage component 220, input component 225, output component 230, and/or communication interface 235.

As shown in FIG. 7, process 700 may include determining an orientation of the UE (block 710). For example, the UE may determine the orientation using at least one gyroscope (e.g., gyroscope 240), as described above. Additionally, or alternatively, the UE may determine the orientation using an ambient light sensor, an accelerometer (e.g., accelerometer 245), and/or another sensor. In some aspects, the orientation may include a portrait orientation, a landscape orientation, and/or another orientation of the UE. Accordingly, the UE may estimate the orientation based at least in part on one or more measurements from the gyroscope, the accelerometer, the ambient light sensor, and/or another sensor.

As further shown in FIG. 7, process 700 may include classifying a grip type associated with the UE (block 720). For example, the UE may classify (e.g., using processor 210) the grip type based at least in part on the orientation, as described above. In some aspects, the UE may apply machine learning to determine the grip type. For example, the UE may use a regression classifier, a neural network, and/or another trained model to classify the grip type based at least in part on measurements from the gyroscope, the accelerometer, the ambient light sensor, and/or another sensor. In some aspects, the classification may include whether the UE is on a body of a user of the UE (e.g., in a hand of the user or balanced on a leg or other limb of the user), in clothing of a user of the UE, and/or in another position. Additionally, or alternatively, the classification may include a one-hand grip in landscape mode (e.g., a right hand grip or a left hand grip), a two-hand grip in landscape mode (e.g., as shown in FIG. 3B), a one-hand grip in portrait mode (e.g., as shown in FIG. 3A), and/or another grip type.

As further shown in FIG. 7, process 700 may include determining one or more grip points associated with the UE (block 730). For example, the UE may determine (e.g., using processor 210) the grip points based at least in part on the orientation and/or the hand grip, as described above. In some aspects, the UE may apply machine learning to determine the grip points. For example, the UE may use a regression classifier, a neural network, and/or another trained model to determine the one or more grip points based at least in part on measurements from the gyroscope, the accelerometer, the ambient light sensor, and/or another sensor.

Based at least in part on the orientation, the grip type, and/or the one or more grip points, the UE may estimate an axis associated with an angular motion of the UE. Accordingly, the UE may use the axis to perform angular and linear movement detection and compensation, as described elsewhere herein.

Process 700 may include additional implementations, such as any single implementation or any combination of implementations described below and/or in connection with one or more other processes described elsewhere herein.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The following provides an overview of some aspects of the present disclosure:

Aspect 1: A method of movement detection performed by a user equipment (UE), comprising: determining an angular motion using at least one gyroscope of the UE; and adjusting at least one measurement from at least one sensor that is associated with the UE and used to measure relative position, based at least in part on the angular motion.

Aspect 2: The method of aspect 1, wherein the relative position is with respect to an external object to be classified as animate or inanimate.

Aspect 3: The method of aspect 2, further comprising: classifying the external object as animate or inanimate based at least in part on the at least one measurement after adjusting.

Aspect 4: The method of any of aspects 1 through 3, wherein the at least one gyroscope is included in at least one inertial measurement unit of the UE.

Aspect 5: The method of any of aspects 1 through 4, wherein determining the angular motion comprises computing an angle from the at least one gyroscope of the UE.

Aspect 6: The method of any of aspects 1 through 5, wherein the angular motion is defined by an amplitude and a phase of angular vibration of the UE.

Aspect 7: The method of any of aspects 1 through 6, further comprising: determining at least one distance between the at least one sensor and an estimated grip associated with the UE.

Aspect 8: The method of aspect 7, further comprising: determining at least one translation associated with the at least one sensor based at least in part on the angular motion and the at least one distance.

Aspect 9: The method of aspect 8, wherein adjusting the at least one measurement comprises offsetting the at least one measurement based at least in part on the at least one translation.

Aspect 10: The method of any of aspects 8 through 9, further comprising: projecting the at least one translation onto a direction associated with the at least one sensor, wherein the at least one measurement is adjusted based at least in part on the projection.

Aspect 11: The method of any of aspects 1 through 10, further comprising: determining at least one linear movement of the UE using at least one measurement from at least one accelerometer of the UE, wherein the at least one measurement from the at least one sensor is adjusted based at least in part on at least one translation associated with the at least one sensor determined from the angular motion and the at least one linear movement.

Aspect 12: The method of aspect 11, wherein the at least one accelerometer is included in at least one inertial measurement unit of the UE.

Aspect 13: The method of any of aspects 11 through 12, wherein determining the at least one linear movement comprises adjusting the at least one measurement from the at least one accelerometer based at least in part on the angular motion and determining the at least one linear movement using the at least one adjusted measurement.

Aspect 14: The method of any of aspects 11 through 13, wherein the at least one linear movement is defined by an amplitude and a phase associated with motion of the UE.

Aspect 15: The method of any of aspects 11 through 14, further comprising: receiving at least one relative distance between the at least one sensor and the at least one accelerometer.

Aspect 16: The method of aspect 15, further comprising: determining at least one translation associated with the at least one sensor based at least in part on the angular motion, the at least one linear movement, and the at least one relative distance.

Aspect 17: The method of aspect 16, further comprising: projecting the at least one translation onto a direction associated with the at least one sensor, wherein the at least one measurement is adjusted based at least in part on the projection.

Aspect 18: The method of any of aspects 1 through 17, wherein the at least one sensor includes a radar device, and wherein adjusting the at least one measurement comprises adjusting a signal from the radar device.

Aspect 19: An apparatus for wireless communication at a device, comprising a processor; memory coupled with the processor; and instructions stored in the memory and executable by the processor to cause the apparatus to perform the method of one or more aspects of aspects 1-18.

Aspect 20: A device for wireless communication, comprising a memory and one or more processors coupled to the memory, the memory and the one or more processors configured to perform the method of one or more aspects of aspects 1-18.

Aspect 21: An apparatus for wireless communication, comprising at least one means for performing the method of one or more aspects of aspects 1-18.

Aspect 22: A non-transitory computer-readable medium storing code for wireless communication, the code comprising instructions executable by a processor to perform the method of one or more aspects of aspects 1-18.

Aspect 23: A non-transitory computer-readable medium storing a set of instructions for wireless communication, the set of instructions comprising one or more instructions that, when executed by one or more processors of a device, cause the device to perform the method of one or more aspects of aspects 1-18.

The foregoing disclosure provides illustration and description, but is not intended to be exhaustive or to limit the aspects to the precise forms disclosed. Modifications and variations may be made in light of the above disclosure or may be acquired from practice of the aspects.

As used herein, the term "component" is intended to be broadly construed as hardware, firmware, and/or a combination of hardware and software. As used herein, a processor is implemented in hardware, firmware, and/or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the aspects. Thus, the operation and behavior of the systems and/or methods were described herein without reference to specific software code—it being understood that software and hardware can be designed to implement the systems and/or methods based, at least in part, on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various aspects. In fact, many of these features may be combined in ways not specifically recited in the claims and/or disclosed in the specification. Although each dependent claim listed below may directly depend on only one claim, the disclosure of various aspects includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the terms "set" and "group" are intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method of movement detection performed by a user equipment (UE), comprising:
    determining one or more grip points associated with the UE based at least in part on a grip type;
    estimating an axis associated with an angular motion based at least in part on the grip type and the one or more grip points
    determining, based at least in part on the axis, the angular motion using at least one gyroscope of the UE;
    adjusting at least one measurement from at least one sensor that is associated with the UE and used to measure relative position, based at least in part on the angular motion, wherein the relative position is with respect to an external object to be classified as animate or inanimate; and
    classifying the external object as animate or inanimate based at least in part on the at least one measurement after adjusting.

2. The method of claim 1, wherein the at least one gyroscope is included in at least one inertial measurement unit of the UE.

3. The method of claim 1, wherein determining the angular motion comprises computing an angle from the at least one gyroscope of the UE.

4. The method of claim 1, wherein the angular motion is defined by an amplitude and a phase of angular vibration of the UE.

5. The method of claim 1, further comprising:
    determining at least one distance between the at least one sensor and an estimated grip associated with the UE.

6. The method of claim 5, further comprising:
    determining at least one translation associated with the at least one sensor based at least in part on the angular motion and the at least one distance.

7. The method of claim 6, wherein adjusting the at least one measurement comprises offsetting the at least one measurement based at least in part on the at least one translation.

8. The method of claim 6, further comprising:
    projecting the at least one translation onto a direction associated with the at least one sensor,
        wherein the at least one measurement is adjusted based at least in part on the projection.

9. The method of claim 1, further comprising:
    determining at least one linear movement of the UE using at least one measurement from at least one accelerometer of the UE,
        wherein the at least one measurement from the at least one sensor is adjusted based at least in part on at least one translation associated with the at least one sensor determined from the angular motion and the at least one linear movement.

10. The method of claim 9, wherein the at least one accelerometer is included in at least one inertial measurement unit of the UE.

11. The method of claim 9, wherein determining the at least one linear movement comprises adjusting the at least one measurement from the at least one accelerometer based at least in part on the angular motion and determining the at least one linear movement using the at least one adjusted measurement.

12. The method of claim 9, wherein the at least one linear movement is defined by an amplitude and a phase associated with motion of the UE.

13. The method of claim 9, further comprising:
    receiving at least one relative distance between the at least one sensor and the at least one accelerometer.

14. The method of claim 13, further comprising:
determining at least one translation associated with the at least one sensor based at least in part on the angular motion, the at least one linear movement, and the at least one relative distance.

15. The method of claim 14, further comprising:
projecting the at least one translation onto a direction associated with the at least one sensor,
wherein the at least one measurement is adjusted based at least in part on the projection.

16. The method of claim 1, wherein the at least one sensor includes a radar device, and wherein adjusting the at least one measurement comprises adjusting a signal from the radar device.

17. The method of claim 1, further comprising:
determining an orientation of the UE; and
classifying the grip type associated with the UE based at least in part on the orientation.

18. A user equipment (UE), comprising:
a memory; and
one or more processors operatively coupled to the memory, the memory and the one or more processors configured to:
determine one or more grip points associated with the UE based at least in part on a grip type;
estimate an axis associated with an angular motion based at least in part on the grip type and the one or more grip points;
determine, based at least in part on the axis, the angular motion using at least one gyroscope of the UE;
adjust at least one measurement from at least one sensor that is associated with the UE and used to measure relative position, based at least in part on the angular motion, wherein the relative position is with respect to an external object to be classified as animate or inanimate; and
classify the external object as animate or inanimate based at least in part on the at least one measurement after adjusting.

19. The UE of claim 18, wherein the at least one gyroscope is included in at least one inertial measurement unit of the UE.

20. The UE of claim 18, wherein the one or more processors, when determining the angular motion, are configured to compute an angle from the at least one gyroscope of the UE.

21. The UE of claim 18, wherein the angular motion is defined by an amplitude and a phase of angular vibration of the UE.

22. The UE of claim 18, wherein the one or more processors are further configured to:
determine at least one distance between the at least one sensor and an estimated grip associated with the UE.

23. The UE of claim 22, wherein the one or more processors are further configured to:
determine at least one translation associated with the at least one sensor based at least in part on the angular motion and the at least one distance.

24. The UE of claim 23, wherein the one or more processors, when adjusting the at least one measurement, are configured to offset the at least one measurement based at least in part on the at least one translation.

25. The UE of claim 23, wherein the one or more processors are further configured to:
project the at least one translation onto a direction associated with the at least one sensor,
wherein the at least one measurement is adjusted based at least in part on the projection.

26. The UE of claim 18, wherein the one or more processors are further configured to:
determine at least one linear movement of the UE using at least one measurement from at least one accelerometer of the UE,
wherein the at least one measurement from the at least one sensor is adjusted based at least in part on at least one translation associated with the at least one sensor determined from the angular motion and the at least one linear movement.

27. The UE of claim 26, wherein the at least one accelerometer is included in at least one inertial measurement unit of the UE.

28. The UE of claim 26, wherein the one or more processors, when determining the at least one linear movement, are configured to adjust the at least one measurement from the at least one accelerometer based at least in part on the angular motion and determine the at least one linear movement using the at least one adjusted measurement.

29. The UE of claim 26, wherein the at least one linear movement is defined by an amplitude and a phase associated with motion of the UE.

30. The UE of claim 26, wherein the one or more processors are further configured to:
receive at least one relative distance between the at least one sensor and the at least one accelerometer.

31. The UE of claim 30, wherein the one or more processors are further configured to:
determine at least one translation associated with the at least one sensor based at least in part on the angular motion, the at least one linear movement, and the at least one relative distance.

32. The UE of claim 31, wherein the one or more processors are further configured to:
project the at least one translation onto a direction associated with the at least one sensor,
wherein the at least one measurement is adjusted based at least in part on the projection.

33. The UE of claim 18, wherein the at least one sensor includes a radar device, and wherein adjusting the at least one measurement comprises adjusting a signal from the radar device.

34. The UE of claim 18, wherein the memory and the one or more processors are further configured to:
determine an orientation of the UE; and
classify the grip type associated with the UE based at least in part on the orientation.

35. A non-transitory computer-readable medium storing a set of instructions for wireless communication, the set of instructions comprising:
one or more instructions that, when executed by one or more processors of a user equipment (UE), cause the UE to:
determine one or more grip points associated with the UE based at least in part on a grip type;
estimate an axis associated with an angular motion based at least in part on the grip type and the one or more grip points;
determine, based at least in part on the axis, the angular motion using at least one gyroscope of the UE;
adjust at least one measurement from at least one sensor that is associated with the UE and used to measure relative position, based at least in part on the angular motion, wherein the relative position is with respect to an external object to be classified as animate or inanimate; and classify the external object as animate or inanimate based at least in part on the at least one measurement after adjusting.

36. An apparatus for wireless communication, comprising:

means for determining one or more grip points associated with the apparatus based at least in part on a grip type;

means for estimating an axis associated with an angular motion based at least in part on the grip type and the one or more grip points;

means for determining, based at least in part on the axis, the angular motion using at least one gyroscope;

means for adjusting at least one measurement from at least one sensor that is associated with the apparatus and used to measure relative position, based at least in part on the angular motion, wherein the relative position is with respect to an external object to be classified as animate or inanimate; and means for classifying the external object as animate or inanimate based at least in part on the at least one measurement after adjusting.

* * * * *